(12) United States Patent
Venkatasubramanian et al.

(10) Patent No.: US 9,314,163 B2
(45) Date of Patent: Apr. 19, 2016

(54) TISSUE SENSING DEVICE FOR SUTURELESS VALVE SELECTION

(71) Applicant: St. Jude Medical, Cardiology Division, Inc., St. Paul, MN (US)

(72) Inventors: Ramji T. Venkatasubramanian, Maplewood, MN (US); Chad Joshua Green, Forest Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 13/753,099

(22) Filed: Jan. 29, 2013

(65) Prior Publication Data

US 2014/0213918 A1    Jul. 31, 2014

(51) Int. Cl.
A61B 5/02 (2006.01)
A61B 5/00 (2006.01)
A61F 2/24 (2006.01)
A61B 5/107 (2006.01)

(52) U.S. Cl.
CPC ......... *A61B 5/02028* (2013.01); *A61B 5/02007* (2013.01); *A61B 5/1076* (2013.01); *A61B 5/4851* (2013.01); *A61B 5/6847* (2013.01); *A61B 5/6869* (2013.01); *A61F 2/2496* (2013.01); *A61B 2562/028* (2013.01); *A61B 2562/0214* (2013.01); *A61B 2562/046* (2013.01)

(58) Field of Classification Search
CPC ........ A61B 5/05; A61B 5/053; A61B 5/0538; A61B 5/02028
USPC ........................................ 600/508
See application file for complete search history.

(56) References Cited

U.S. PATENT DOCUMENTS

| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Joseph Dietrich
(74) *Attorney, Agent, or Firm* — Lerner, David, Littenberg, Krumholz & Mentlik, LLP

(57) ABSTRACT

A sensing device for a collapsible prosthetic heart valve, the sensing device including an elongated shaft having a proximal end and a distal end, a sensing body coupled to the distal end of the shaft, the sensing body being adapted to fit within a native valve annulus and at least one microelectromechanical sensor attached to the sensing body, the at least one sensing body being capable of measuring a property of tissue.

24 Claims, 10 Drawing Sheets

(56) References Cited

U.S. PATENT DOCUMENTS

| | | | |
|---|---|---|---|
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0009746 A1* | 1/2008 | Forster et al. | 600/467 |
| 2008/0021552 A1 | 1/2008 | Gabbay | |
| 2008/0039934 A1 | 2/2008 | Styrc | |
| 2008/0051838 A1* | 2/2008 | Shuros et al. | 607/2 |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0160832 A1 | 6/2010 | Braido | |
| 2010/0168778 A1 | 7/2010 | Braido | |
| 2010/0168836 A1 | 7/2010 | Kassab | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2014/0180277 A1* | 6/2014 | Chen | 606/41 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |

(56) References Cited

FOREIGN PATENT DOCUMENTS

| | | | |
|---|---|---|---|
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2006073626 | A2 | 7/2006 |
| WO | 2007071436 | A2 | 6/2007 |
| WO | 2008042347 | A2 | 4/2008 |
| WO | 2008070797 | A2 | 6/2008 |
| WO | 2010008548 | A2 | 1/2010 |
| WO | 2010043982 | A2 | 4/2010 |
| WO | 2010070633 | A1 | 6/2010 |
| WO | 2010096176 | A1 | 8/2010 |
| WO | 2010098857 | A1 | 9/2010 |

OTHER PUBLICATIONS

Design U.S. Appl. No. 29/375,243, filed Sep. 20, 2010.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR (powerpoint)—dated May 25, 2010?
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
International Search Report and Written Opinion for Application No. PCT/US2014/012240 dated Apr. 15, 2014.

\* cited by examiner

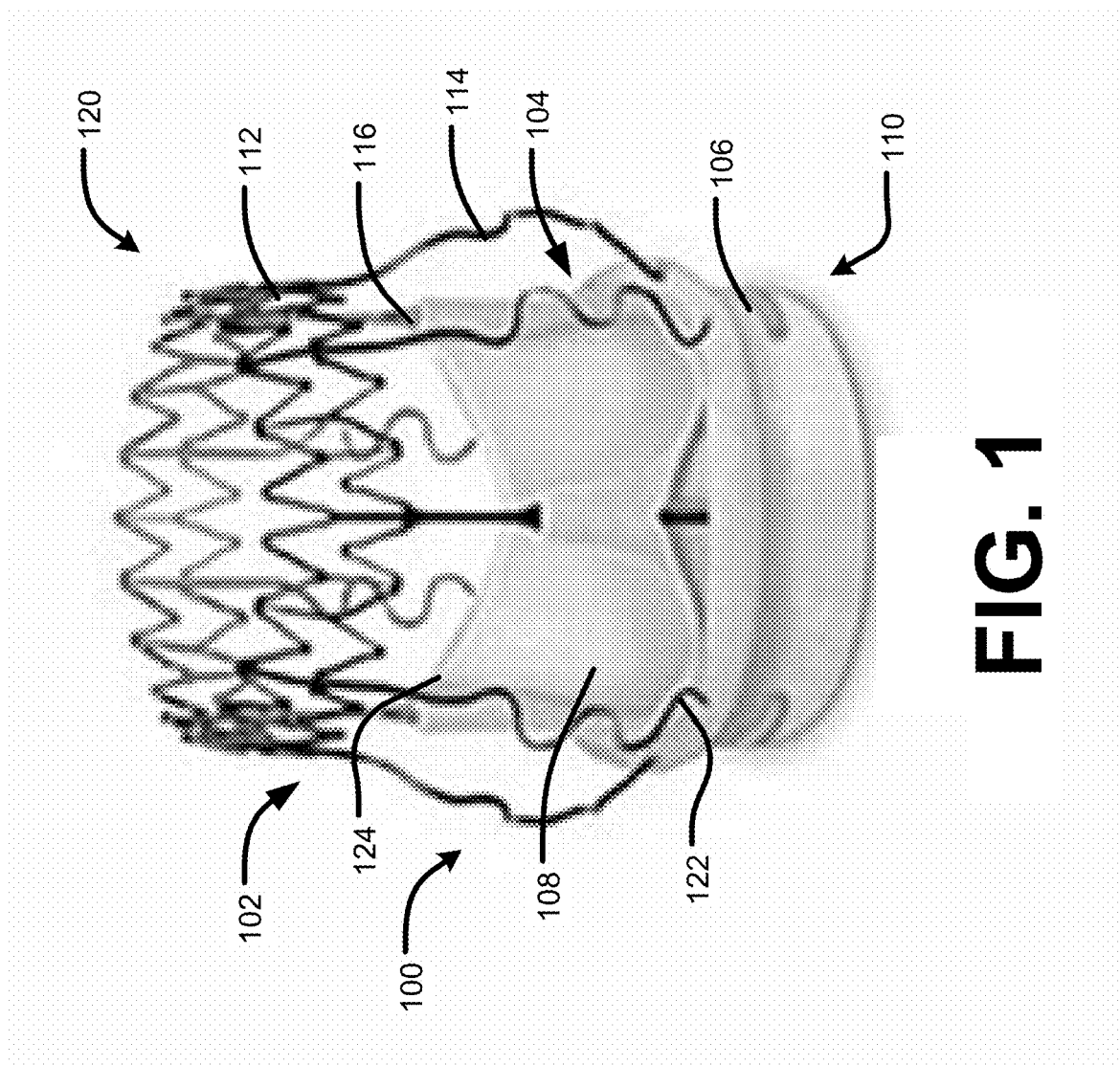

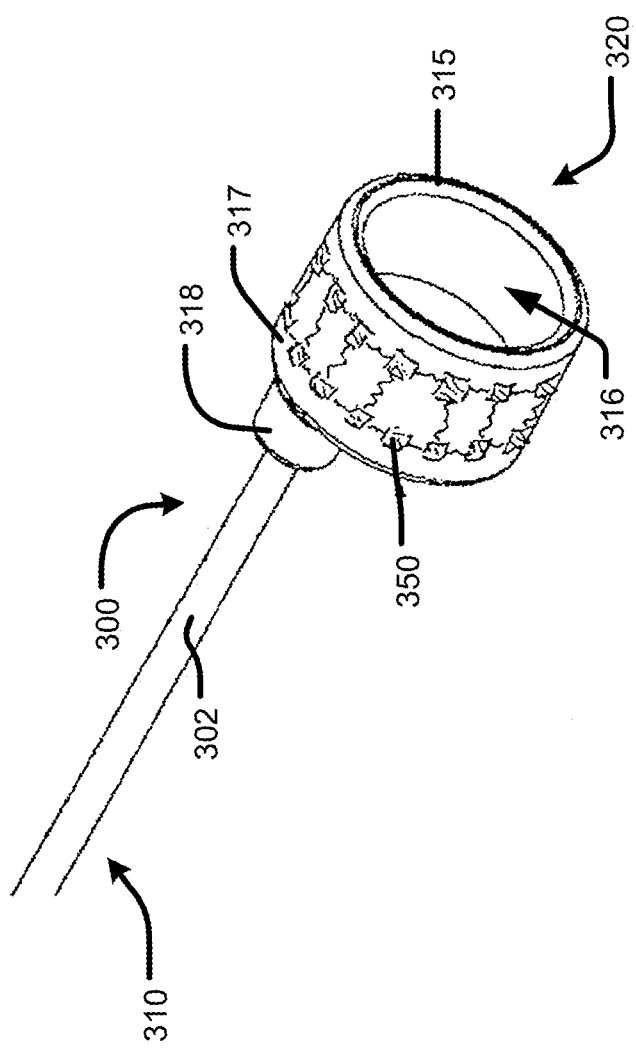

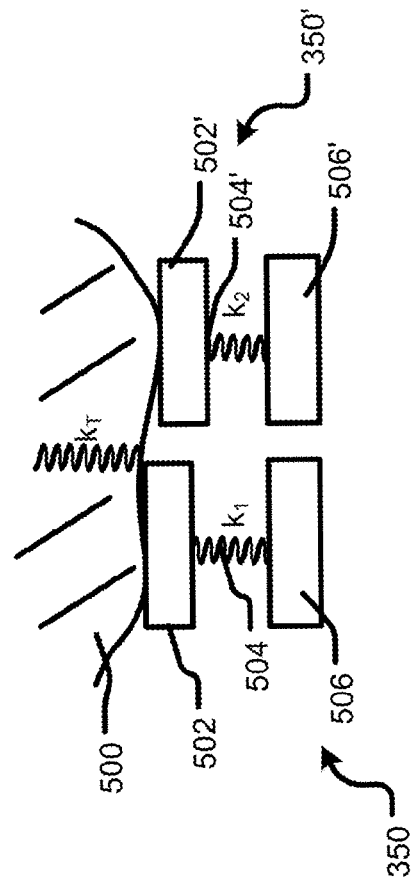
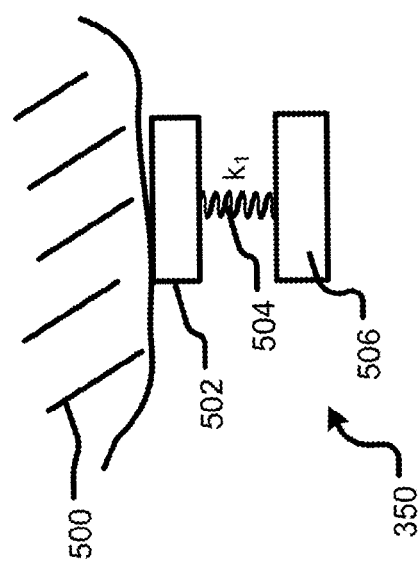

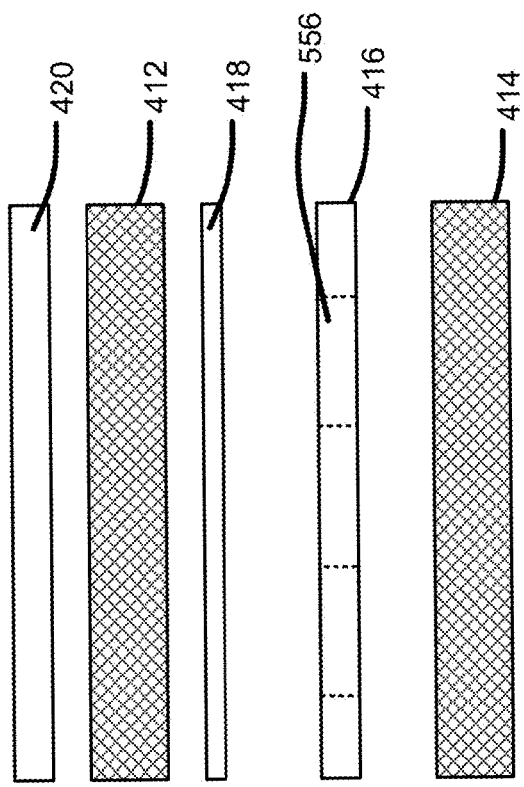
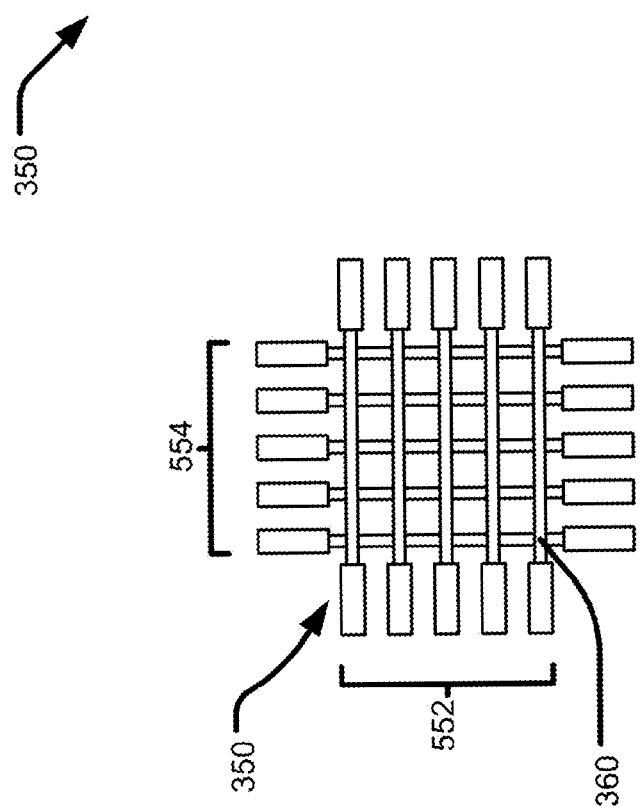
FIG. 5B
FIG. 5A

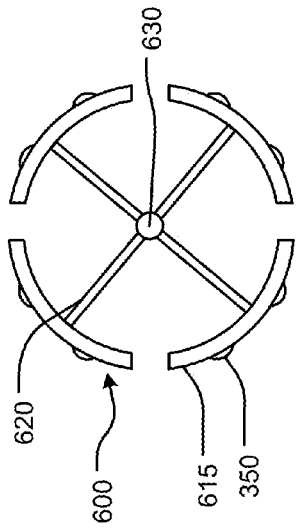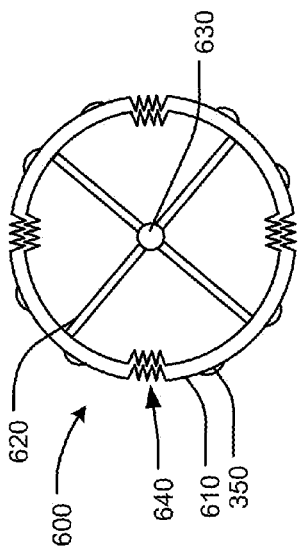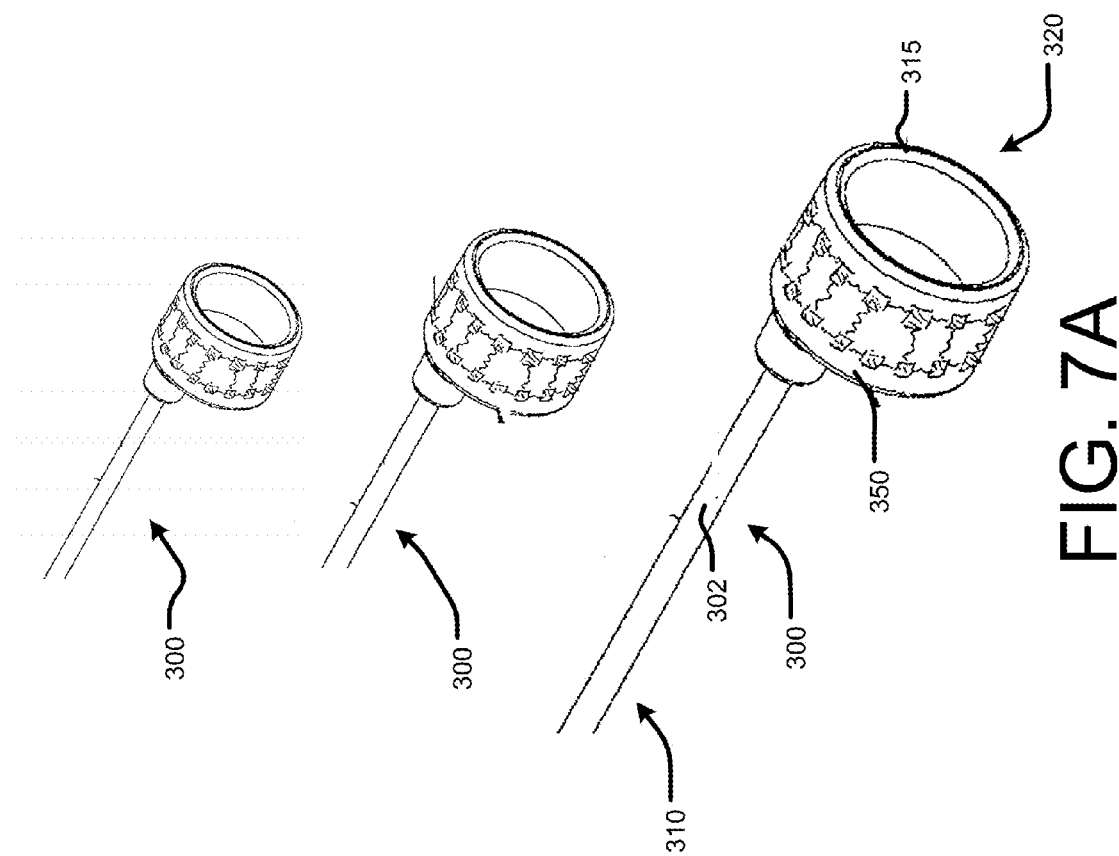

TISSUE SENSING DEVICE FOR SUTURELESS VALVE SELECTION

BACKGROUND OF THE INVENTION

The present invention relates to heart valve replacement and, in particular, to sutureless prosthetic heart valves. More particularly, the present invention relates to systems, devices and methods for sizing and for identifying optimal decalcification levels at an annulus site prior to positioning of sutureless prosthetic heart valves.

Prosthetic heart valves may generally belong to one of three categories: surgical valves, transcatheter valves and sutureless valves. Transcatheter valves are typically collapsible to a relatively small circumferential size and can be delivered into a patient less invasively than valves that are not collapsible. A collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

In contrast to transcatheter valves, surgical valves and sutureless valves are typically delivered to a patient via open-heart surgery. Surgical valves are usually delivered to the site of implant and a portion of the surgical valve, typically an outer rim, is sutured to patient tissue. Sutureless valves, on the other hand, typically include a stent to anchor the valve in place instead of sutures. Because sutureless valves do not require lengthy suturing to patient anatomy, they are generally implanted in less time than surgical valves, resulting in less time on a bypass machine and a reduced risk of infection.

Despite the various improvements that have been made to the sutureless prosthetic heart valve implantation process, conventional methods of implanting heart valves suffer from some shortcomings. For example, in conventional techniques, clinical success of a heart valve is dependent on accurate deployment, anchoring and acceptable valve performance. Inaccurate sizing and positioning of the heart valve decreases performance and increases risks such as heart valve migration, which may result in severe complications due to obstruction of the left ventricular outflow tract and may even result in patient death. Additionally, the extent of calcification of the implant site may also affect performance. For example, calcification of the aortic valve may affect anchoring within the native aortic valve annulus such as by causing ovalization of the implanted valve which can lead to paravalvular leaks. The interaction between the implanted valve and the calcified tissue is believed to be relevant, in addition to anchoring the valve in place, to preventing valve migration and leakage.

Without being bound to any particular theory, it is believed that improper anchoring of the valve may occur due to a mismatch between the size of the native annulus and the size of the prosthetic valve (e.g., using a small heart valve size in a large annulus), lower calcification levels in the native tissue than actually predicted, or improper positioning of the valve resulting in insufficient expansion of the valve diameter. Moreover, overestimation of the annulus size may cause an oversized valve to be implanted, leading to local complications in the, for example, the aortic root, including coronary orifice obstruction, aortic dissection and heart blockage. Additionally, oversized valves may cause extended compression and/or stent deformation that affects valve durability.

In addition, incorrect sizing of a valve due to anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, systems, methods and devices are desirable that would reduce the likelihood of removal. Systems, methods and devices are also desirable to reduce negative side effects caused by improper anchoring.

Current methods for estimating the size of a patient's anatomy include imaging techniques such as transthoracic echocardiograms, trans-esophageal echocardiograms and angiography. These imaging methods are not standardized and may yield inconsistent results due to the elliptical shape of the target anatomy. Additionally, none of these techniques allow for contact forces between the annulus and stent to be measured and do not account for calcification.

There, therefore, is a need for further improvements to the devices, systems, and methods for positioning and anchoring of prosthetic heart valves. Specifically, there is a need for further improvements to the devices, systems, and methods for accurately measuring the native annulus dimensions and calcification levels in a patient. In particular, there is the need to be able to identify optimal decalcification levels at an annulus site prior to a valve implant so as to maximize valve durability by reducing the degree of ovalization and minimize the risk of migration ensuring safe anchoring of the valve due to the presence of sufficient calcification. Such accurate measurement will thus help to reduce the risks associated with valve migration and improper valve positioning. Among other advantages, the present invention may address one or more of these needs.

BRIEF SUMMARY OF THE INVENTION

In some embodiments, a sensing device for measuring a property of tissue for selecting a collapsible prosthetic heart valve may include an elongated shaft having a proximal end and a distal end. A body may be coupled to the distal end of the shaft, the body being adapted to fit within a native valve annulus. At least one microelectromechanical sensor may be attached to the body, the at least one sensor being capable of measuring a property of tissue adjacent to the native valve annulus.

In some examples, the body may be comprised of a hollow cylindrical body having an outer surface and the at least one microelectromechanical sensor is disposed on the outer surface of the cylindrical body. The at least one sensor may be capable of obtaining data relating to native valve annulus diameter. The at least one sensor may be capable of obtaining data relating to the extent of calcification of tissue. The at least one sensor may include at least one capacitor. The at least one sensor may include piezoelectric material. A plurality of sensors may be arranged about the body. The plurality of sensors may be arranged in a matrix of a plurality of rows and columns which are evenly spaced apart both circumferentially and longitudinally about the body. The plurality of sensors may be arranged in a matrix of a plurality of rows and columns which are unevenly spaced apart both circumferentially and longitudinally about the body. The shaft may be radially offset from a central axis of the body.

In some embodiments, a method for measuring a property of tissue for selecting a collapsible prosthetic heart valve may include introducing a device to the native annulus. The device may include (i) a body adapted to fit within a native valve annulus and having a first diameter and (ii) at least one microelectromechanical sensor attached to the body capable of measuring a property of tissue. Data related to a property of tissue adjacent the native annulus responsive to the at least one microelectromechanical sensor may be obtained.

In some examples, the data may relate to an annulus diameter. The data may relate to an extent of calcification. The obtained data may be a measurement of a contact force between the tissue and the at least one microelectromechanical sensor. The at least one sensor may include a plurality of sensors arranged about the body, the plurality of sensors being configured to measure elasticity of the tissue.

In some examples, the method may further include the step of comparing the obtained data to a dataset that includes a relationship between elasticity and blood pressure. The method may further include comparing the obtained data to a dataset that includes a relationship between valve diameter and blood pressure. The device may then be removed from the native annulus.

In some embodiments, a system of measuring a property of tissue for selecting a collapsible prosthetic heart valve may include a device having (i) a body adapted to fit within a native valve annulus, and (ii) at least one microelectromechanical sensor attached to the body, the at least one sensor being capable of measuring a property of tissue adjacent to the native valve annulus, a memory for storing a predefined dataset, and a processor for using the predefined dataset and information received from the at least one sensor for determining a property of the tissue.

In some examples, the predefined dataset may include relationships between blood pressure and desired calcification for a given valve size. The predefined dataset may include relationships between blood pressure and desired contact forces for a given valve size.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

FIG. 1 is a perspective view of a conventional sutureless prosthetic heart valve;

FIG. 3 is a perspective view of a tissue sensing device according to one embodiment of the present invention;

FIG. 4A is a schematic view illustrating the principles of operation of a single microelectromechanical sensor;

FIG. 4B is a schematic view illustrating the principles of operation of multiple sensors;

FIG. 5A is a top plan view of a microelectromechanical sensor array in accordance with an embodiment of the present invention;

FIG. 5B is a close-up of a sensor structure of FIG. 5A with separated layers in accordance with an embodiment of the present invention;

FIG. 7A is a perspective view of a several examples of the tissue sensing devices in accordance with one embodiment of the present invention;

FIG. 7B illustrates an adjustable tissue sensing device in accordance with another embodiment of the present invention;

FIG. 7C illustrates an adjustable tissue sensing device having accordion portions accordance with another embodiment of the present invention;

DETAILED DESCRIPTION

Figure 2A:
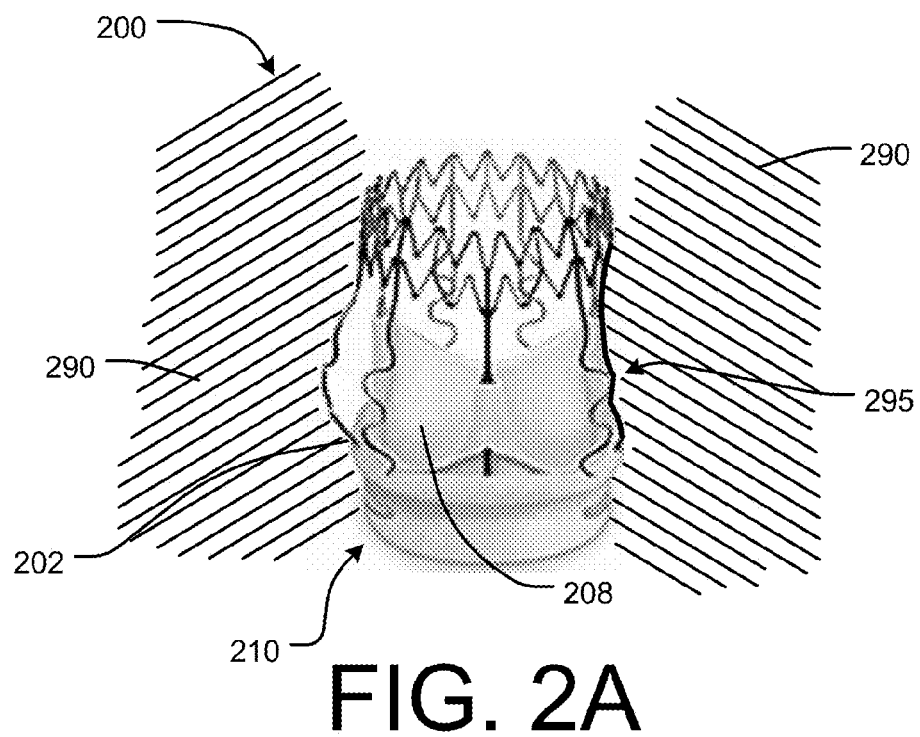
FIG. 2A is a perspective view illustrating the sutureless heart valve of FIG. 1 having poor fitment in a native valve annulus.

As used herein, the term "proximal," when used in connection with a prosthetic heart valve, refers to the portion or end of the heart valve closest to the heart when the heart valve is implanted in a patient, whereas the term "distal," when used in connection with a prosthetic heart valve, refers to the portion or end of the heart valve farthest from the heart when the heart valve is implanted in a patient. When used in connection with devices for delivering or sizing a prosthetic heart valve into a patient, the terms "proximal" and "distal" are to be taken as relative to the user of the devices. "Proximal" is to be understood as relatively close to the user, and "distal" is to be understood as relatively farther away from the user.

In describing the preferred embodiments of the invention illustrated in the drawings, specific terminology will be used for the sake of clarity. However, the invention is not intended to be limited to the specific terms so used, and it is to be understood that each specific term includes all equivalents that operate in a similar manner to accomplish a similar purpose.

FIG. 1 shows a conventional sutureless heart valve 100. The prosthetic heart valve 100 is designed to replace the function of a native aortic valve of a patient. Although the invention is described herein as applied to a prosthetic heart valve for replacing a native aortic valve, the invention is not so limited, and may be applied to other prosthetic valves, such as for example, other cardiac applications.

The sutureless prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section 120. The annulus section 110 and the aortic section 120 of stent 102 may include a plurality of cells 112 connected to one another around the stent. The annulus section 110 and the aortic section 120 of the stent 102 may include one or more annular rows of cells 112 connected to one another. For instance, the annulus section 110 may have two annular rows of cells 112. Regardless of its shape, each cell 112 is formed by a plurality of struts 114.

The stent 102 may include commissure points 116 disposed on or near certain struts 114. The commissure points 116 may include eyelets for facilitating the suturing of a valve assembly 104 to the sent 102.

The sutureless prosthetic heart valve 100 also includes a valve assembly 104 attached inside the annulus section 110 of the stent 102. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the cuff 106 or the stent 102 by any suitable attachment means, such as suturing, stapling, adhesives or the like. For example, the first edge 122 of each leaflet 108 may be attached to the cuff 106, and the cuff may in turn be attached to the stent 102. Alternatively, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve.

In operation, the embodiment of the sutureless prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed on the end of a delivery device and delivered during open-heart surgery. Once the delivery device has reached the target site, the user may deploy the sutureless heart valve. Upon deployment, the sutureless heart valve expands, preferably into secure engagement within the native aortic annulus. The delivery device may then be retracted out of the chest cavity and the chest incision closed. When the prosthetic heart valve is properly positioned inside the heart, it works as a one-way valve, allowing blood to flow in one direction and preventing blood from flowing in the opposite direction.

Problems may be encountered when implanting the sutureless prosthetic heart valve. For example, in certain procedures, heart valves may be implanted in a native valve annulus without first resecting the native valve leaflets. The valves may have critical clinical issues because of the nature of the stenotic leaflets that are left in place. Additionally, patients with uneven calcification, bi-cuspid aortic valve disease, and/or valve insufficiency may not be treated well, if at all, with current valve designs.

Additionally, the reliance on unevenly calcified leaflets for proper valve placement and seating could lead to several problems, such as: (1) paravalvular leakage (i.e., leakage between the prosthetic implant and the native anatomy), (2) valve migration, (3) mitral valve impingement, (4) conduction system disruption, (5) coronary blockage, etc., all of which can have severely adverse clinical outcomes. To reduce these adverse events, a valve should seal and anchor adequately without the need for excessive radial force, protrusion into the left ventricular outflow tract (LVOT), etc., that could harm nearby anatomy and physiology.

FIG. 2A is a schematic illustrating a sutureless heart valve 200 having poor fitment within native valve annulus 290. Specifically, the annulus section 210 of the stent 202 is distorted near deformed portion 295. Improper fitment of the sutureless heart valve 200 may lead to any of the problems discussed above. In addition, as the stent 202 of collapsible prosthetic heart valve 200 distorts during implantation, during beating of the heart, or because of irregularities in the patient's anatomy or the condition of the native valve, such distortion may be translated to the valve assembly, such that not all of the valve leaflets 208 meet to form effective coaptation junctions. This can result in leakage or regurgitation and other inefficiencies which can reduce cardiac performance. Moreover, if the prosthetic valve 200 is not placed optimally and the valve leaflets 208 are not coapting as intended, other long term effects, such as uneven wear of the individual leaflets 208, can be postulated. Such improper fitment may be due to poor positioning, disregard for calcification or use of the wrong valve size.

Figure 2B:
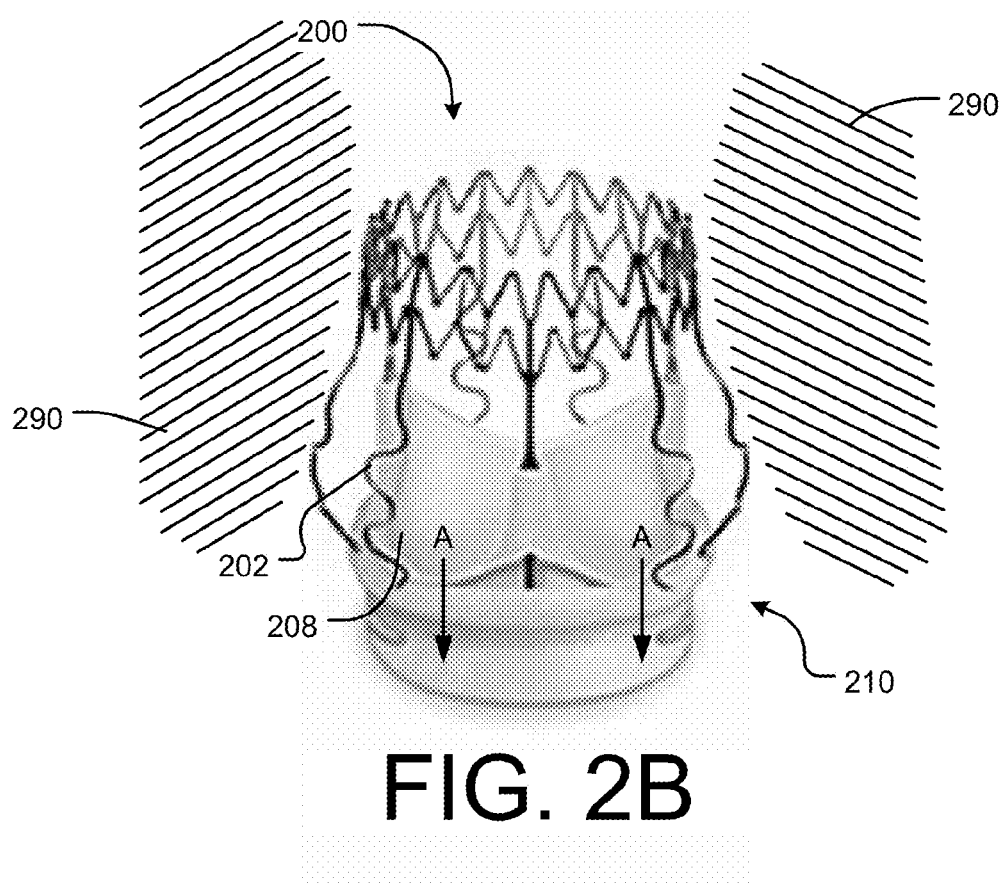
FIG. 2B is a perspective view illustrating the sutureless heart valve of FIG. 1 that has migrated from its implantation position in the native valve annulus.

Poor positioning, disregard for calcification or the use of the wrong valve size may also cause heart valve migration. As seen in FIG. 2B, prosthetic heart valve 200 has partially translated into the ventricle from its intended location at native valve annulus 290, a condition that may lead to a host of problems as discussed above. Even a small shift in position as indicated by arrows "A" may cause inadequate sealing and improper valve function. Migration may also result in inadequate coaptation leading to regurgitation of blood passing through the valve.

In order to avoid these problems, a tissue sensing device may be used to accurately determine the annulus diameter and the calcification levels (e.g., tissue elasticity) in the aortic valve. The tissue sensing device may be deployed first within the native valve sinus (e.g., an aortic root) to determine the size, shape and condition of the sinus. After obtaining sufficient measurements, the tissue sensing device may be removed from the native valve sinus and the native valve sinus decalcified as desired. A suitable prosthetic heart valve may then be chosen based on the obtained measurements. The selected prosthetic heart valve may then be implanted with a reduced risk of deformation and/or migration, as well as ovalization which could lead to paravalvular leaks.

FIG. 3 illustrates a tissue sensing device 300 according to one embodiment of the present invention. The tissue sensing device 300 has a proximal end 310 and a distal end 320 and may include an elongated shaft 302 disposed near the distal end 320. Elongated shaft 302 may be formed of a metal such as nitinol, stainless steel or any other malleable material capable of being bent by the user to facilitate access to the sizing site. Shaft 302 may be coupled to a sensing body 315 as shown in FIG. 3. The sensing body 315 in accordance with one embodiment of the present invention is constructed from a hollow cylindrical body having a through opening 316 to allow for visualization through the sizer during use of the sensing body. The surrounding wall 317 of the sensing body has a generally planar outer peripheral surface. The shaft 302 may be fixedly or removably attached to the sensing body 315 by means of a connector 318. As shown, the longitudinal axis of the shaft 302 is arranged spaced from and generally parallel to the longitudinal center axis of the cylindrical body forming sensing body 315. In another embodiment (not shown), the longitudinal axis of the shaft 302 may be aligned with the center longitudinal axis of the cylindrical body forming the sensing body 315. In this regard, a plurality of spokes (not shown) would be provided within the opening 316 formed by the sensing body 315 to support the connector 318 for attachment to the shaft 302.

Sensing body 315 may be formed of a rigid material such as polysulfone or polyphenylsufone or other suitable materials, such as, for example, polycarbonate, polyetherimide or polyamides. Although the sensing body 315 is illustrated as being cylindrical, it will be understood that different shapes for sensing body 315 may be possible such as, for example, spheroid or a prism.

A plurality of sensors 350 may be coupled to the periphery of sensing body 315 at various points and in various patterns on the wall 317 of the sensing body so that they are capable of contacting body tissue. Sensors 350 may be coupled to sensing body 315 by being embedded around the periphery of sensing body 315 or coupled using a bioadhesive or any other suitable method. It will be understood that more than one sensor 350 may be coupled to sensing body 315 as seen in the illustrated embodiments. For example, two or three sensors 350 may be evenly disposed about the outer circumference of sensing body 315. The sensors 350 may be also be disposed in two or more rows about the circumference of sensing body 315 as seen in FIG. 3. In the preferred embodiment, the sensors 350 are arranged in a matrix of a plurality of rows and columns which may be evenly spaced apart, or unevenly spaced apart, both circumferentially and longitudinally about the sensing body 315. For example, the sensing body 315 may include a matrix of two rows and twelve columns of sensors 350, or more or less rows and/or columns depending on the size of the sensing body as used for a particular patient. In at least some examples, sensors 350 may be individually identified so that measurements obtained by the sensors 350 may be mapped to their location.

In one embodiment, sensors 350 may include piezoelectric sensors, optical sensors, electromagnetic sensors, capacitive sensors and the like positioned around the periphery of sensing body 315 to measure a force applied to the sensor by the native valve annulus. By way of example, a FLEXIFORCE® sensor made by TEKSCAN® may be used to measure force.

By inserting the sensing body 315 within a native valve annulus, the radial force against the sensors may be measured. FIG. 4A illustrates use of a force sensor according to this embodiment. Though FIG. 4A illustrates a sensor having a spring, this example is merely illustrative and it will be understood that the sensor may be any of those described above as well as other sensors known in the art. A sensor 350 may include a contacting member 502, a spring 504 and a base layer 506. Spring 504 may be connected to both the contacting member 502 and the base layer 506 and disposed between the two. The sensor 350 may be positioned near target tissue 500 and, as can be appreciated from FIG. 4A, brought in contact with tissue 500, with contacting member 502 abutting the tissue. As the sensor 350 is gradually advanced, spring 504 begins to compress. Knowing the spring constant kl of spring 504, the force against contacting member 502 may be measured.

This measured radial force may be compared against valves in a lookup table or database that provides adequate radial force for valves of varying diameter. These values may be obtained by in vitro testing. In at least some examples, the table or database may also include information relating to blood pressure to adjust for variations in blood pressure. Specifically, patients with higher blood pressure (e.g., 200 mm Hg) may suggest the need for greater radial forces for adequate anchoring while patients with lower blood pressure (e.g., 100 mm Hg or less) may call for lower radial forces. By way of illustration, a measurement between about 0.50 N and about 2.00 N may suggest that the proper size for a valve has been identified. If the measurement is below 0.50 N, then a larger sensing body should be used. If the measurement is above 2.00 N, then a smaller sensing body should be used. Thus, this process may be repeated until the correct valve size is determined.

In a second embodiment, multiple sensors may be located near one another to acquire information relating to elasticity of the surrounding tissue. FIG. 4B shows the concept of using a sensor 350 to measure calcification of tissue by measuring the tissue elasticity. A sensor 350 may include a contacting member 502, a spring 504 and a base layer 506. A second sensor 350 may include a contacting member 502', a spring 504' and a base layer 506'. Each spring 504,504' may be connected to its respective contacting member 502,502' and base layer 506,506' and disposed between the two. Moreover, sensors 350,350' may be positioned near target tissue 500 and, as can be appreciated from FIG. 4B, brought in contact with tissue 500, with contacting members 502,502' abutting the tissue. As the sensors 350,350' are gradually advanced, springs 504 and 504' begin to compress.

Springs 504 and 504' may have different spring constants. As shown in FIG. 4B, spring 504 has a spring constant of kl and spring 504' has a spring constant of $k_2$. Additionally, the stiffness of tissue 500 may be represented by a spring having a spring constant $k_T$. By pushing contacting members 502, 502' against tissue 500, the springs 504 and 504' will have different amounts of deflection based on the different spring constants. Specifically, spring 504' having a lower spring constant will suffer a greater deflection compared to its counterpart as shown in the figure on the right. The relative deflection of the springs may then be used to calculate the tissue stiffness represented by $k_2$. This may then be used to analyze the extent of calcification of the tissue and, to decalcify the tissue to a suitable level and to choose the appropriate prosthetic heart valve for implanting in the patient. Thus, by examining the force exerted on springs 504 and 504' and the displacement of both springs, the stiffness of tissue 500 may be determined. The stiffness of the tissue may then be used to select the appropriate valve or appropriate level of calcification needed as will be described in greater detail with reference to the algorithms and methods below.

In a third embodiment, microelectromechanical sensors may be used to measure the extent of calcification of a tissue. Details of these sensors will be fully discussed with reference to FIGS. 5A, 5B and 6A-C. In this embodiment, sensor 350 may be a microelectromechanical sensor and may include, but is not limited to, sensors capable of measuring capacitance, piezoelectricity or any other suitable parameter. Sensor 350 may also include a flexible tactile microelectromechanical sensor. One example of such sensor is known in the art and described in "Flexible Tactile Sensor For Tissue Elasticity Measurements," Journal of Microelectromechanical Systems, Vol. 19, No. 6, December 2009, the contents of which are hereby incorporated in its entirety as if fully recited herein.

FIGS. 5A and 5B illustrate one possible configuration of a suitable microelectromechanical sensor 350. Sensor 350 may be flexible and deformable in order to collect information about size, shape and calcification of the native aortic valve. In that regard, sensor 350 may be fashioned from fabric or flexible polymer layers such as polydimethylsiloxane (PDMS) or a polyimide having capacitors.

In one example, PDMS may be chosen as the structural material due to its advantageous properties such as flexibility, ductility, and biocompatibility. The biological and medical compatibility of the material has been well documented. Moreover, PDMS devices can be readily sterilized for medical applications. In addition, PDMS is mechanically much softer than other polymer materials commonly utilized in microfabrication.

FIG. 5A illustrates a PDMS sensor array consisting of 5×5 capacitors 360, the operation of which will be described in greater detail with reference to FIGS. 6B and 6C. In order to minimize the wiring interfaces, the top and bottom electrodes may be oriented in orthogonal directions.

As seen in FIG. 5A, the intersection of wires forms each capacitor 360. A close-up of the sensor structure with separated layers is shown in FIG. 5B. Embedded electrodes are built on a top PDMS layer 412 and a bottom PDMS layer 414. A spacer layer 416 is sandwiched between the electrodes and defines air gaps 556. An insulation layer 418 may also be used to prevent the shorting of electrodes which could be the consequence when large deflection of sensing diaphragms occurs. Finally, a bump layer 420 is utilized to transfer contact forces through the air gap to be measured by capacitive change.

Figure 6A:
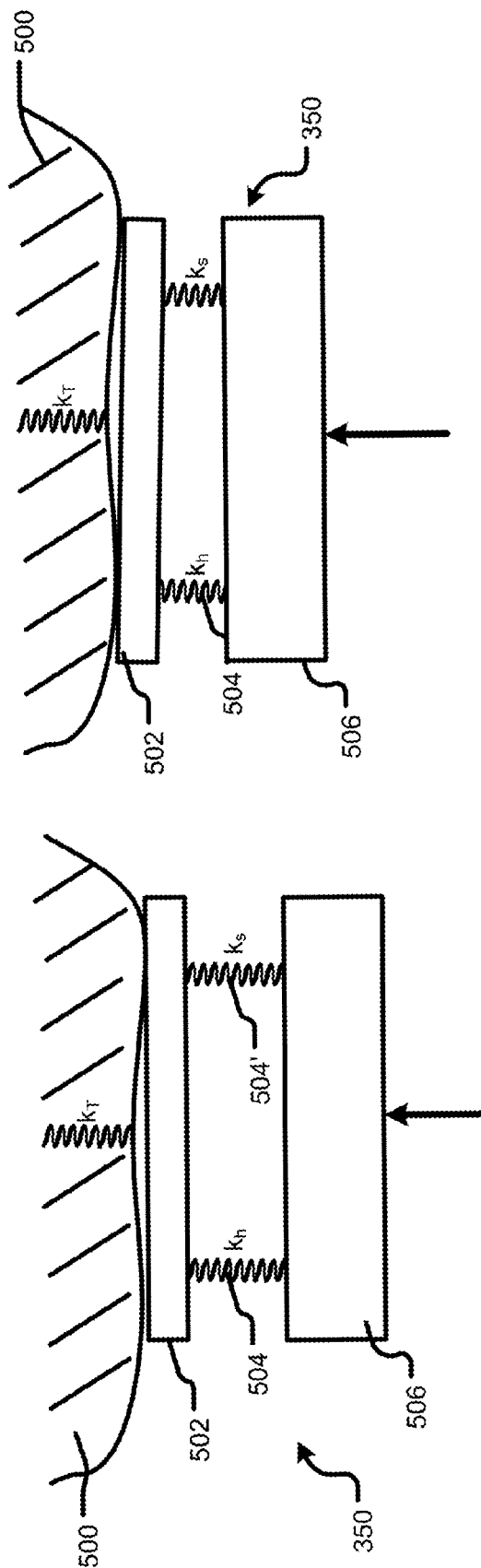
FIG. 6A is a schematic view illustrating the principles of operation of a microelectromechanical sensor.

In order to illustrate the principle of operation of the invention, FIG. 6A shows the concept of using a sensor 350 to measure calcification of tissue by measuring the tissue elasticity. A sensor 350 may include a contacting member 502, a pair of springs 504 and 504' and a base layer 506. Springs 504 and 504' may be connected to both the contacting member 502 and the base layer 506 and disposed between the two. The sensor 350 may be positioned near target tissue 500 and, as can be appreciated from FIG. 6A, brought in contact with tissue 500, with contacting member 502 abutting the tissue. As the sensor 350 is gradually advanced, springs 504 and 504' begin to compress.

Springs 504 and 504' may have different spring constants. As shown in FIG. 6A, spring 504 has a spring constant of kh and spring 504' has a spring constant of $k_s$. Additionally, the stiffness of tissue 500 may be represented by a spring having a spring constant $k_T$. By pushing contacting member 502 against tissue 500, the springs 504 and 504' will have different amounts of deflection based on the different spring constants. Specifically, spring 504' having a lower spring constant will suffer a greater deflection compared to its counterpart as shown in the figure on the right. The relative deflection of the springs may then be used to calculate the tissue stiffness represented by $k_T$. This may then be used to analyze the extent of calcification of the tissue and, to decalcify the tissue to a suitable level and to choose the appropriate prosthetic heart valve for implanting in the patient. Thus, by examining the force exerted on springs 504 and 504' and the displacement of both springs, the stiffness of tissue 500 may be determined.

Figure 6B:
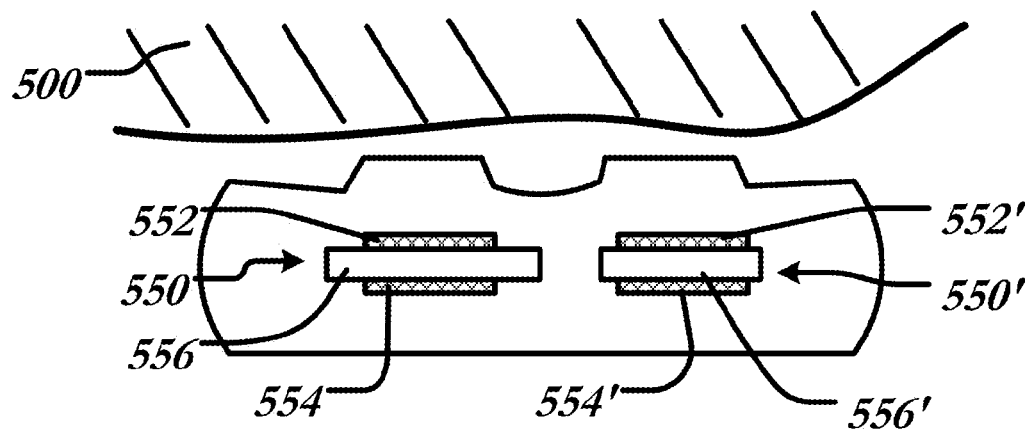
FIGS. 6B and 6C are schematic views illustrating a microelectromechanical sensor formed of a capacitative pair.
Figure 6C:
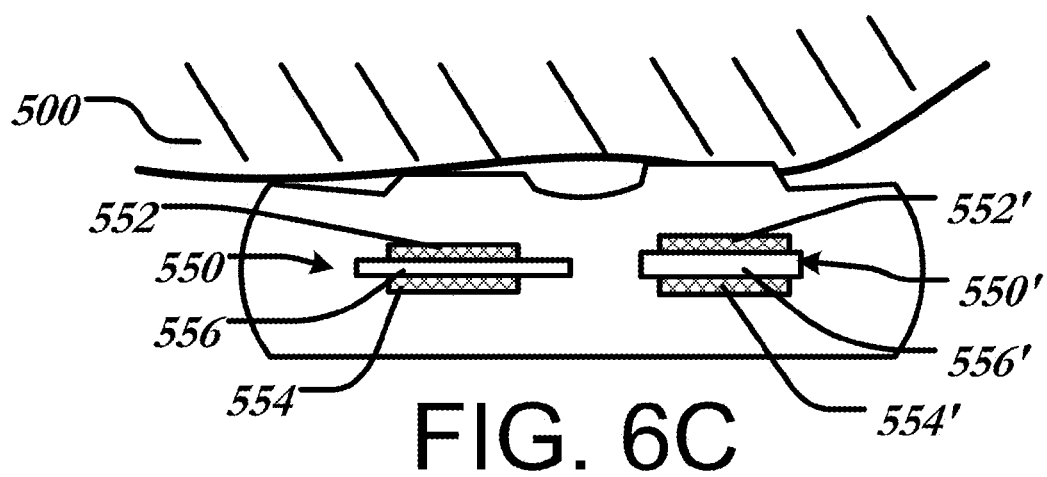

In one embodiment of implementing this concept, a capacitor pair for the sensors 350 may be used, as shown in FIGS. 6B and 6C. As shown in these figures, capacitor 550 includes a first top electrode 552, a first bottom electrode 554 and a first air gap 556 to form a first capacitor. A second capacitor is formed of a second top electrode 552', a second bottom electrode 554' and a second air gap 556' disposed between the second top electrode and the second bottom electrode. As seen in FIG. 6B, air gaps 556 and 556' are formed of varying areas analogous to the different springs discussed above with reference to FIG. 6A. When the sensor is contacted by tissue 500 as seen in FIG. 6B, relative deflection may be precisely measured by the capacitive change of each element as shown in FIG. 6C. The ratio of deflection (based on the capacitive change of each capacitor) may then be compared against valves in tables or graphs of known relationships between deflection change ratios and material stiffness. This information can then be further processed to classify the degree of calcification.

As seen in FIG. 7A, sensing devices 300 may be formed with sensing bodies 315 having different diameters for accurately obtaining measurements relating to the annulus diameter and/or calcification using sensors 350. For examples, sensing bodies 315 may be formed in sizes ranging from 17.0 mm to 31.0 mm. The difference between each sequential sensing body may be about 2.00 mm. For example, sensing device 300 may include a plurality of sensing bodies 315 having diameters of 17.0, 19.0, 21.0, and 23.0 mm or sensing devices that correspond to some of the most popular sizes for aortic valves such as 19.0, 21.0, 23.0 and 25.0 mm.

In another example, instead of multiple sensing device 300, an adjustable sensing device may be utilized. As seen in FIG. 7B, adjustable sensing device 600 may include a plurality of sensors 350 may be disposed on a sensing body 610 formed of a series of body segments 615. Each segment 615 may form a portion of a cylindrical body and be coupled to a shaft 302 via a spoke 620. Each of spokes 620 may be connected to a central hub 630 which extends in a longitudinal direction and is disposed at the center of segments 615. Space may be disposed within each body segment 615 so that the diameter of sensing device 300 may be adjusted. Radial expansion and contraction of sensing device 300 may be accomplished by manipulation of spokes 620 using a device as described in U.S. Patent Application No. 2008/0306586, the contents of which are incorporated herein in its entirety as if fully set herein. In an alternative embodiment, shown in FIG. 7C, instead of discontinuous body segments, sensing body 610 may include a substantially cylindrical body and any number of accordion portions 640. Accordion portions 640 may allow radial adjustment of sensing body 610.

Figure 8:
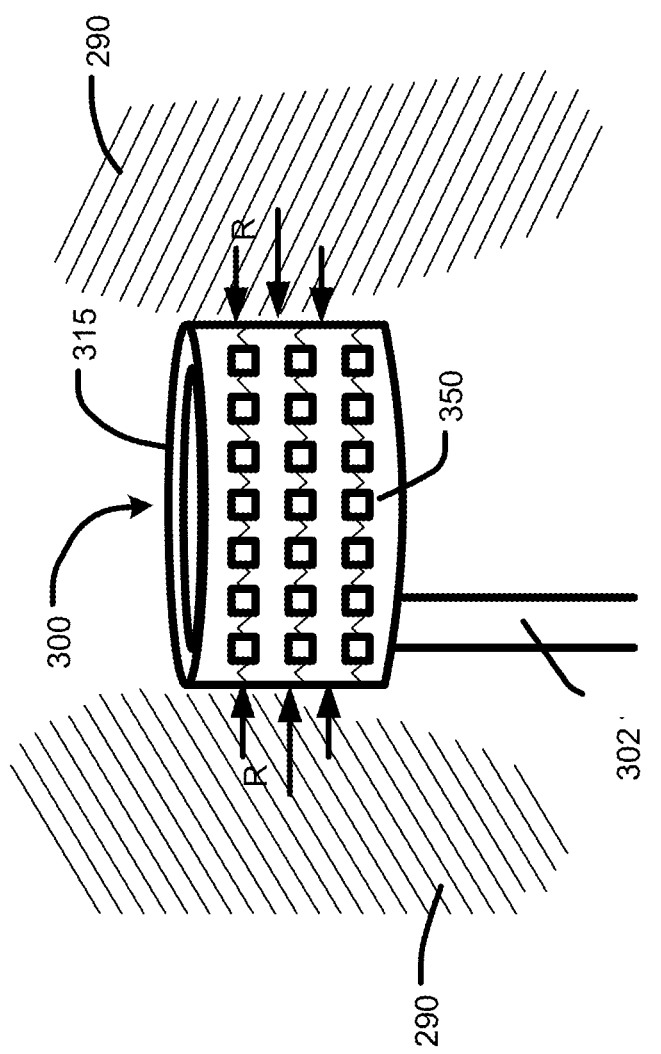
FIG. 8 is an enlarged view of the tissue sensing device of FIG. 3 disposed within the anatomy.

FIG. 8 illustrates a sensing device 300 having a plurality of sensors 350 disposed on a hollow cylindrical sensing body 315 that is adapted to measure contact forces R exerted by the wall of native valve annulus 290 against sensing body 315. Contact forces R may cause corresponding deformation in sensors 350 and relay information relating to annulus diameter and/or calcification. In examples where the leaflets have not been resected, sensing body 315 may be capable of measuring contact forces exerted by the native valve leaflets on sensing body 315.

The following will describe the use of sensing device 300 for sizing, positioning and selecting an appropriate prosthetic heart valve. As an initial step, after opening the chest cavity, but prior to insertion of the prosthetic heart valve, the physician may select a sensing device 300 having a first diameter. The initial sensing device may, for example, be a sensing device 300 having a sensing body 315 of outer diameter of 21.0 mm. Using shaft 302, the physician may advance the sensing device 300 to the annulus so that the sensing body 315 is at the desired site for valve replacement. For example, for aortic valve replacement, the sensing device 300 may be inserted into the site of the native aortic valve.

Once sensing device 300 has reached the desired site of measurement, sensors 350 may gather information relating to capacitance and the change of capacitance at each capacitor. After sufficient data has been collected, the deflection of each capacitor can be determined. The ratio of the relative deflection of each capacitor is correlated to Young's modulus of the contact tissue and may provide information related to tissue stiffness.

Information related to tissue stiffness may be useful in determining properly implanting and anchoring the valve. Too little calcification may lead to valve migration as shown in FIG. 2B while too much calcification may lead to ovalization shown in FIG. 2A. Thus, the measured tissue stiffness may be compared to valves in a lookup table, which provides information relating to valve size (e.g., outer diameter), preferred elasticity range and blood pressure. In one example, a computer may include these and similar data in a memory and may include a processor that performs an algorithm to automatically determine tissue stiffness based on relative capacitive change (and thus relative deflection). Moreover, knowing the tissue stiffness, the algorithm may determine the extent of calcification and if present, whether the amount of calcification is suitable for proper valve performance of a given valve. The algorithm may further provide information or prompts to further decalcify the native valve annulus if too much calcification is present. Additionally, an algorithm may indicate the risk of valve migration and paravalvular leak based on the tissue stiffness and annulus diameter, either through a computer of a handheld mobile device. Furthermore, the algorithm may prompt the user to input the patient's blood pressure and use this information to determine the suitability of the calcification in the native valve annulus.

The sensing device 300 may thus be removed from the patient's body and the collected data used to select the appropriate prosthetic valve size and the prosthetic valve may be deployed and anchored at the selected site using any manner known in the art.

If it appears that the selected sensing device 300 did not collect sufficient data within the annulus because its diameter was too small, a sensing device 300 having a larger diameter may be selected and inserted for gathering data. If, however, the measurements indicate that the sensing body diameter is too large (e.g., measured deflection or force is too high) or that the sensing body 315 is being inserted into the annulus with difficulty, a smaller sensing body 315 may be selected. Once the proper sensing body 315 has been found, the physician may then select a prosthetic heart valve or device corresponding to this sensing device 300 and implant it within the patient.

Figure 9:
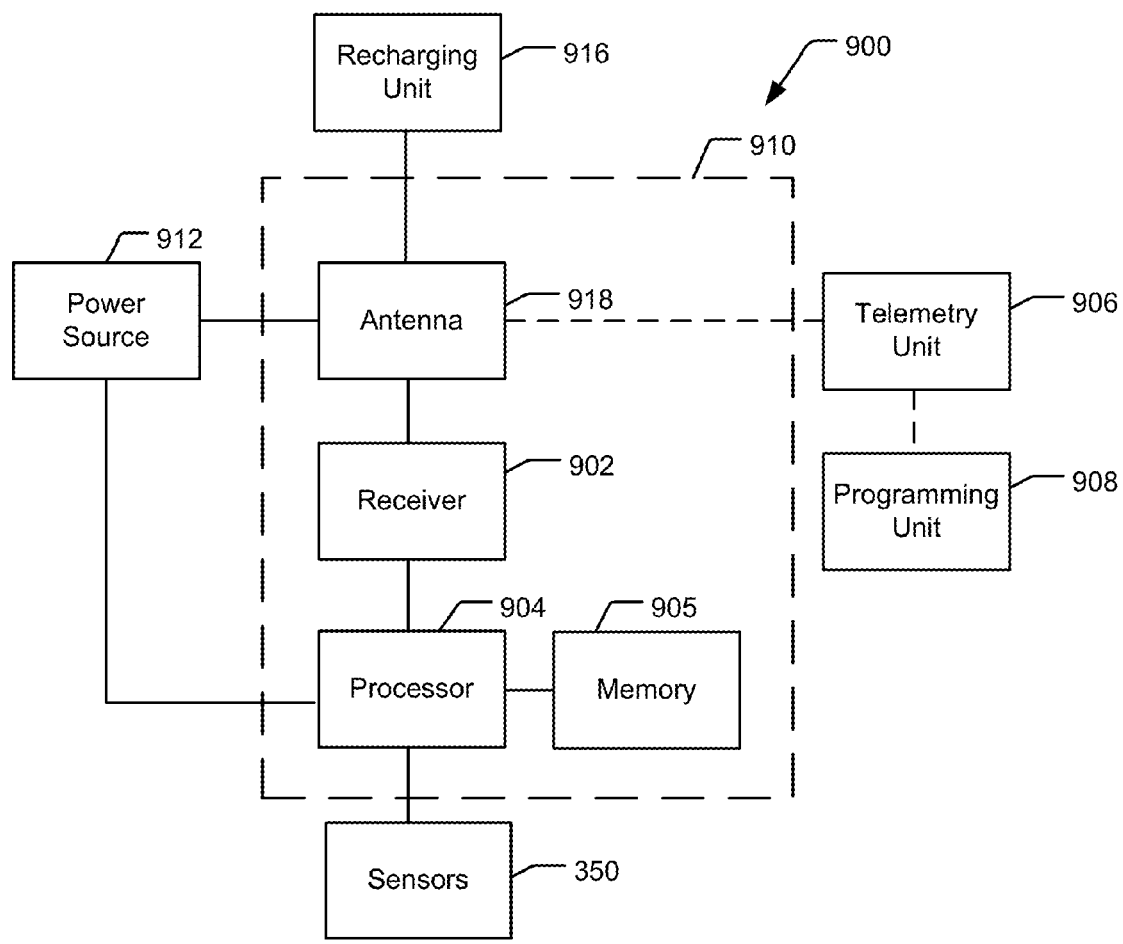
FIG. 9 is a schematic representation of a system for sutureless valve selection.

Sensing device 300 may be included as one component in a system for sizing. FIG. 9 is a schematic overview of one embodiment of components of valve sizing system 900 including an electronic subassembly 910 disposed within a control module. It will be understood that the valve sizing system can include more, fewer, or different components and can have a variety of different configurations including those configurations disclosed in the stimulator references cited herein.

Some of the components (for example, power source 912, antenna 918, receiver 902, and processor 904) of the valve sizing system can be positioned on one or more circuit boards or similar carriers. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like.

If the power source 912 is a rechargeable battery, the battery may be recharged using the optional antenna 918, if desired. Power can be provided to the battery for recharging by inductively coupling the battery through the antenna to a recharging unit 916 external to the user.

A processor 904 is included to obtain data from the sensors relating to force, pressure or elasticity measured by each of the sensors. Any processor can be used and can be as simple as an electronic device that, for example, is capable of receiving and interpreting instructions from an external programming unit 908 and for performing calculations based on the various algorithms described above. A memory 905 may include data in the form of a dataset for performing various steps of the algorithm. For example, in some examples, data from sensors 350 relating to elasticity and data from a programming unit 908 relating to blood pressure may be passed to processor 904 and compared against a dataset stored in memory 905 to determine the appropriate valve size. Additionally, data relating to valve size may be sent from programming unit 908 to processor 904 and the processor may determine the appropriate level of calcification.

While the operation of the sensing device 300 has been described, it will be understood that other embodiments described below may be implemented in a similar manner. It will be understood that combinations of these embodiments may be possible. For example, a sensing body 315 may include any number of sensors and may be separable from shaft 302. It will also be noted that while the inventions herein are predominately described in connection with the replacement of a tricuspid valve, the inventions are equally applicable to the replacement of other valves, including a bicuspid valve, such as the mitral valve as well as other implantable medical devices such as annuloplasty rings and for general measurements of vasculature for delivery of catheters.

Moreover, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A sensing device for measuring a property of tissue for selecting a collapsible prosthetic heart valve, the sensing device comprising:
an elongated shaft having a proximal end and a distal end;
a rigid body having an outer surface, the body being coupled to the distal end of the shaft, the body being adapted to fit within a native valve annulus; and
at least one microelectromechanical sensor attached to the body and being disposed on the outer surface of the body, the at least one sensor having a deflectable portion and being capable of measuring a property of tissue adjacent to the native valve annulus by contacting the tissue against the deflectable portion.

2. The device of claim 1, wherein the body is cylindrical.

3. The device of claim 1, wherein the at least one sensor is capable of obtaining data relating to native valve annulus diameter.

4. The device of claim 1, wherein the at least one sensor is capable of obtaining data relating to the elasticity of tissue.

5. The device of claim 1, wherein the at least one sensor comprises at least one capacitor.

6. The device of claim 1, wherein the at least one sensor includes piezoelectric material.

7. The device of claim 1, further comprising a plurality of sensors arranged about the body.

8. The device of claim 7, wherein the plurality of sensors are arranged in a matrix of a plurality of rows and columns which are evenly spaced apart both circumferentially and longitudinally about the body.

9. The device of claim 7, wherein the plurality of sensors are arranged in a matrix of a plurality of rows and columns which are unevenly spaced apart both circumferentially and longitudinally about the body.

10. The device of claim 1, wherein the shaft is radially offset from a central axis of the body.

11. The device of claim 1, wherein the at least one sensor is configured to collect force data by contacting the tissue.

12. A method for measuring a property of tissue for selecting a collapsible prosthetic heart valve, comprising:
   introducing a device to the native annulus, the device comprising (i) a rigid body having an outer surface and adapted to fit within a native valve annulus and having a first diameter and (ii) at least one microelectromechanical sensor that is attached to the body and disposed on the outer surface thereof, the at least one microelectromechanical sensor being capable of measuring a property of tissue and having a deformable portion; and
   obtaining data related to a property of tissue adjacent the native annulus by contacting the deformable portion of the microelectromechanical sensor with the tissue.

13. The method of claim 12, wherein the data relates to an annulus diameter.

14. The method of claim 12, wherein the obtained data is measurement of a contact force between the tissue and the at least one microelectromechanical sensor.

15. The method of claim 12, wherein the at least one sensor comprises a plurality of sensors arranged about the body, the plurality of sensors being configured to measure elasticity of the tissue.

16. The method of claim 12, further comprising comparing the obtained data to a dataset that includes a relationship between elasticity and blood pressure.

17. The method of claim 12, further comprising comparing the obtained data to a dataset that includes a relationship between valve diameter and blood pressure.

18. The method of claim 12, further comprising removing the device from the native annulus.

19. A system of measuring a property of tissue for selecting a collapsible prosthetic heart valve, the system comprising:
   a device having (i) a rigid body having an outer surface and adapted to fit within a native valve annulus, and (ii) at least one microelectromechanical sensor attached to the body and disposed on the outer surface of the body, the at least one sensor having a deformable portion and being capable of measuring a property of tissue adjacent to the native valve annulus by contacting the tissue;
   a memory for storing a predefined dataset; and
   a processor for using the predefined dataset and information received from the at least one sensor for determining a property of the tissue.

20. The system of claim 19, wherein the predefined dataset includes relationships between blood pressure and desired calcification for a given valve size.

21. The system of claim 19, wherein the predefined dataset includes relationships between blood pressure and desired contact forces for a given valve size.

22. A sensing device for measuring a property of tissue for selecting a collapsible prosthetic heart valve, the sensing device comprising:
   an elongated shaft having a proximal end and a distal end;
   a body coupled to the distal end of the shaft, the body being adapted to fit within a native valve annulus; and
   at least one microelectromechanical sensor having a deflectable portion and being attached to the body, each of the at least one sensor being capable of independently measuring, with respect to others, a property of tissue adjacent to the native valve annulus by contacting the tissue against the deflectable portion.

23. A method for measuring a property of tissue for selecting a collapsible prosthetic heart valve, comprising:
   introducing a device to the native annulus, the device comprising (i) a body adapted to fit within a native valve annulus and having a first diameter and (ii) at least one microelectromechanical sensor that is attached to the body, each of the at least one sensor being capable of independently measuring, with respect to others, a property of tissue, and having a deformable portion; and
   independently obtaining data related to a property of tissue adjacent the native annulus with each of the at least one microelectromechanical sensor by contacting the deformable portion of the sensor with the tissue.

24. A system of measuring a property of tissue for selecting a collapsible prosthetic heart valve, the system comprising:
   a device having (i) a body adapted to fit within a native valve annulus, and (ii) at least one microelectromechanical sensor attached to the body and having a deformable portion, each of the at least one sensor being capable of independently measuring, with respect to others, a property of tissue adjacent to the native valve annulus by contacting the tissue against the deformable portion;
   a memory for storing a predefined dataset; and
   a processor for using the predefined dataset and information received from the at least one sensor for determining a property of the tissue.

\* \* \* \* \*